United States Patent
Bui et al.

(10) Patent No.: US 6,201,752 B1
(45) Date of Patent: Mar. 13, 2001

(54) TIMING CIRCUIT FOR HIGH VOLTAGE TESTING

(75) Inventors: Anh Bui; Scott E. Smith; Duy-Loan T. Le, all of Sugar Land, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 09/398,240

(22) Filed: Sep. 20, 1999

Related U.S. Application Data

(60) Provisional application No. 60/102,703, filed on Oct. 1, 1998.

(51) Int. Cl.[7] ....................................................... G11C 7/00
(52) U.S. Cl. ............................ 365/226; 365/194; 365/191
(58) Field of Search .................................. 365/226, 194, 365/241, 196, 233, 191

(56) References Cited

U.S. PATENT DOCUMENTS 5,996,096 * 11/1999 Dell et al. ............................. 714/710
6,115,319 * 9/2000 Kimoshita et al. .................. 365/233

* cited by examiner

Primary Examiner—Trong Phan
Assistant Examiner—Thong Le
(74) Attorney, Agent, or Firm—Robert N. Roundtree; Frederick J. Telecky, Jr.

(57) ABSTRACT

A circuit is designed with a detector circuit (700) coupled between a supply voltage terminal (705) and a reference voltage terminal (755). The detector circuit produces a first control signal in response to a detected mode and produces a second control signal in response to another mode. A first circuit (205, 207) including a delay circuit receives the first control signal and a third control signal. The delay circuit produces a fourth control signal at an output terminal (215) in response to the first and third control signals. A second circuit (203) receives the second control signal and the third control signal. The second circuit produces the fourth control signal at the output terminal in response to the second and third control signals.

33 Claims, 6 Drawing Sheets

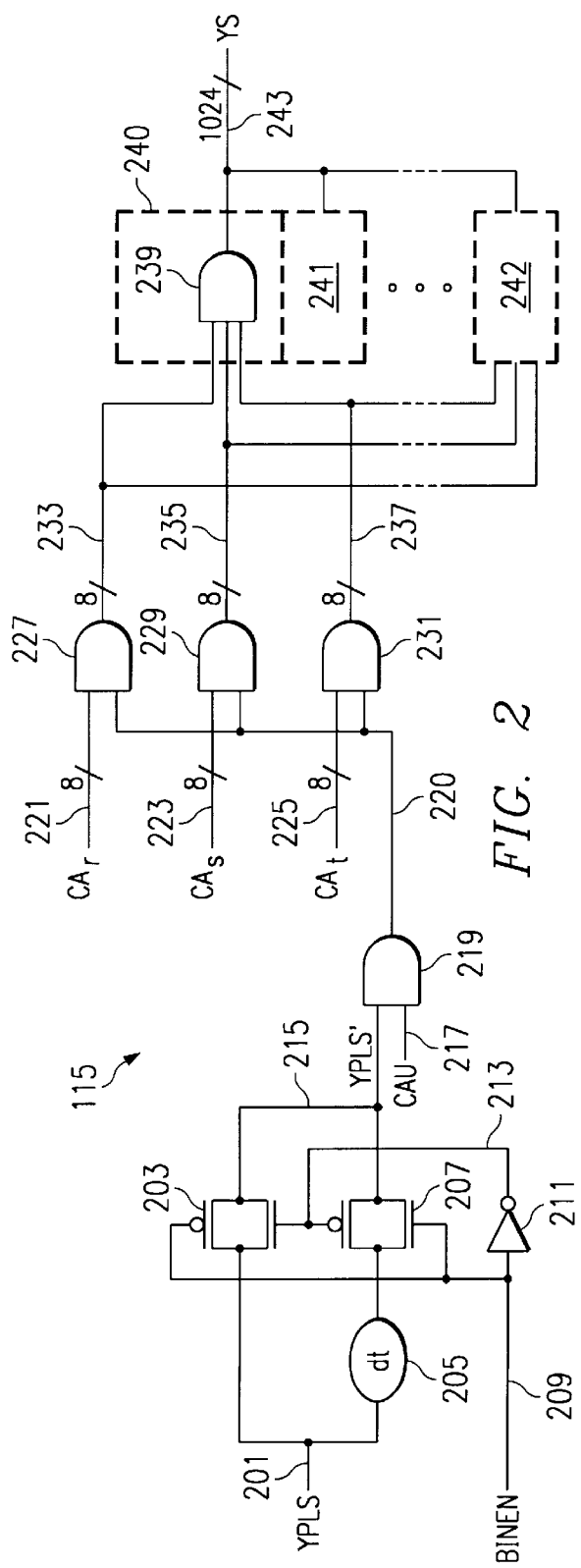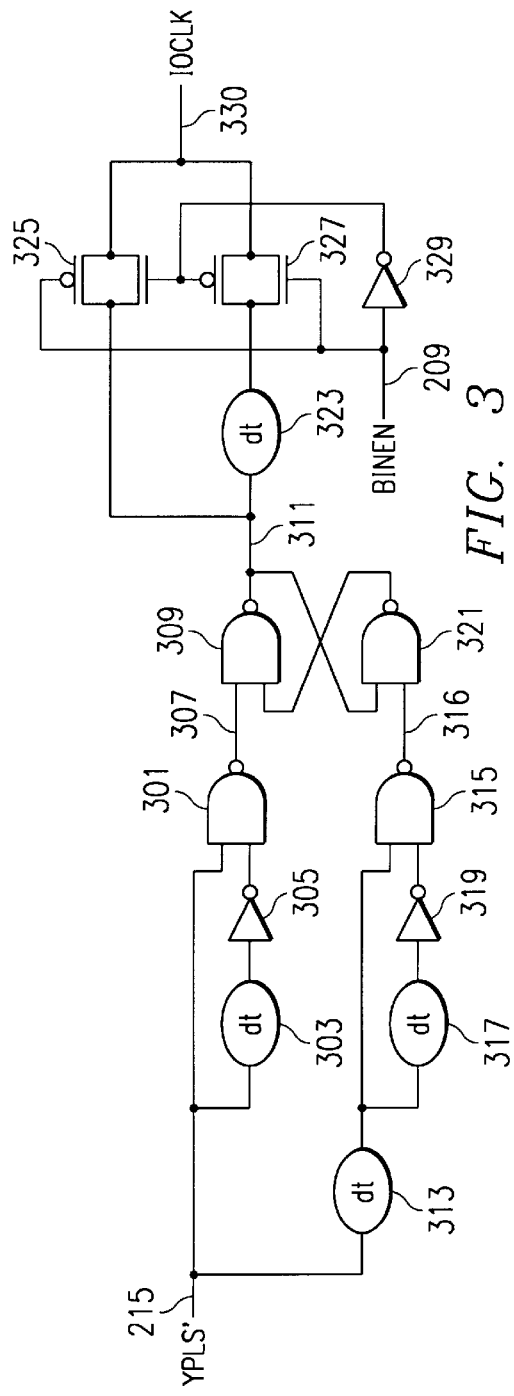

US 6,201,752 B1

TIMING CIRCUIT FOR HIGH VOLTAGE TESTING

This application claims priority under 35 USC § 119(e)(1) of provisional application No. 60/102,073, filed Oct. 1, 1998.

FIELD OF THE INVENTION

This invention relates to an integrated circuit and more particularly to an integrated circuit with a timing circuit for high voltage testing.

BACKGROUND OF THE INVENTION

Present complementary metal oxide semiconductor (CMOS) synchronous dynamic random access memory (SDRAM) circuits are frequently used for main memory in a variety of applications including desk top and portable computer systems. Advances in system technology require ever increasing clock rates and memory bus widths to achieve high data rates. These high data rates, however, are subject to practical limitations. An optimal memory circuit designed for a normal range of supply voltage and temperature may fail to operate correctly under high voltage and high temperature conditions required by a burn in test. A memory circuit functioning at a normal high voltage and high temperature limit of 3.6 V and 90° C., for example, may fail to operate at a burn in condition of 6.5 V and 125° C.

A particular failure mode occurs when a word line is activated and initial data from a memory cell is applied to complementary bit lines. A column decode circuit prematurely couples a selected column to a data lead before a sense amplifier amplifies the data. This premature coupling is due to the increased operating speed at the 6.5 V supply voltage. Moreover, a second data amplifier is also activated prematurely due to increased operating speed and incorrectly reads the data on the data lead. Thus, an optimal design for normal operating conditions may fail a burn in test. A reduction in burn in conditions would result in an inordinate increase in burn in test time. Alternatively, a relaxation in circuit timing would greatly compromise circuit performance under normal operating conditions.

SUMMARY OF THE INVENTION

These problems are resolved by a circuit with a detector circuit coupled between a supply voltage terminal and a reference voltage terminal. The detector circuit produces a first control signal in response to a detected mode and a second control signal in response to another mode. A first circuit including a delay circuit receives the first control signal and a third control signal. The first circuit produces a fourth control signal at an output terminal in response to the first and third control signals. A second circuit receives the second control signal and the third control signal. The second circuit produces the fourth control signal to the output terminal in response to the second and third control signals.

The present invention provides a normal and a delayed control signal for activating a data path. The delayed control signal compensates for circuit operation at high voltage.

BRIEF DESCRIPTION OF THE DRAWINGS

A more complete understanding of the invention may be gained by reading the subsequent detailed description with reference to the drawings wherein:

FIG. 2 is a schematic diagram of an embodiment of a column decode circuit having a timing circuit of the present invention;

FIG. 3 is a schematic diagram of a clock circuit having a timing circuit of the present invention;

DETAILED DESCRIPTION OF THE PREFERRED EMBODIMENTS

Figure 1:
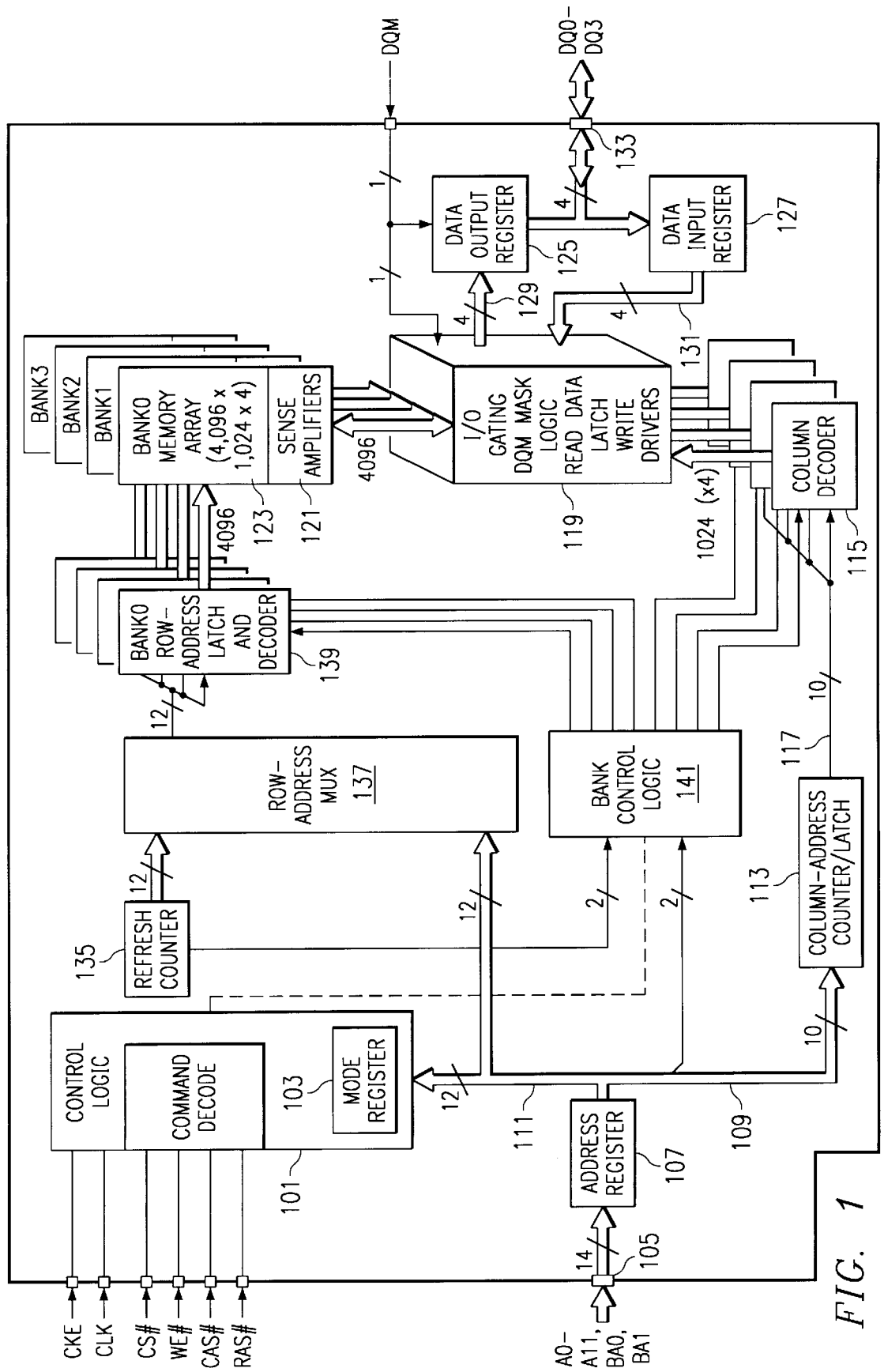
FIG. 1 is a block diagram of a memory system, that may employ a timing circuit according to the present invention.

Referring now to FIG. 1, there is a functional block diagram of a synchronous dynamic random access memory circuit that may employ a timing circuit of the present invention. A control logic circuit 101 receives external signals such as clock enable signal CKE, system clock signal CLK, row address strobe RAS# and column address strobe CAS#. The memory circuit address register 107 receives external address signals at terminals 105. These address signals are applied to mode register 103 to specify various operational modes. The address signals are also applied to row address mux 137, bank control logic 141 and column address counter/latch 113 for accessing specific memory cells. Bank control logic 141 selects one of bank1-bank3 123. Row address latch and decode circuits 139 select a particular row of memory cells within the selected bank. Sense amplifiers 121 then amplify data from memory cells along the particular row. Column decode circuits then decode column address signals on bus 117 to couple selected columns of memory cells along the particular row to respective data leads via I/O gating logic 119. The data leads then conduct data to output terminals 133 via data output register 125 and from output terminals 133 via data input register 127.

Figure 7:
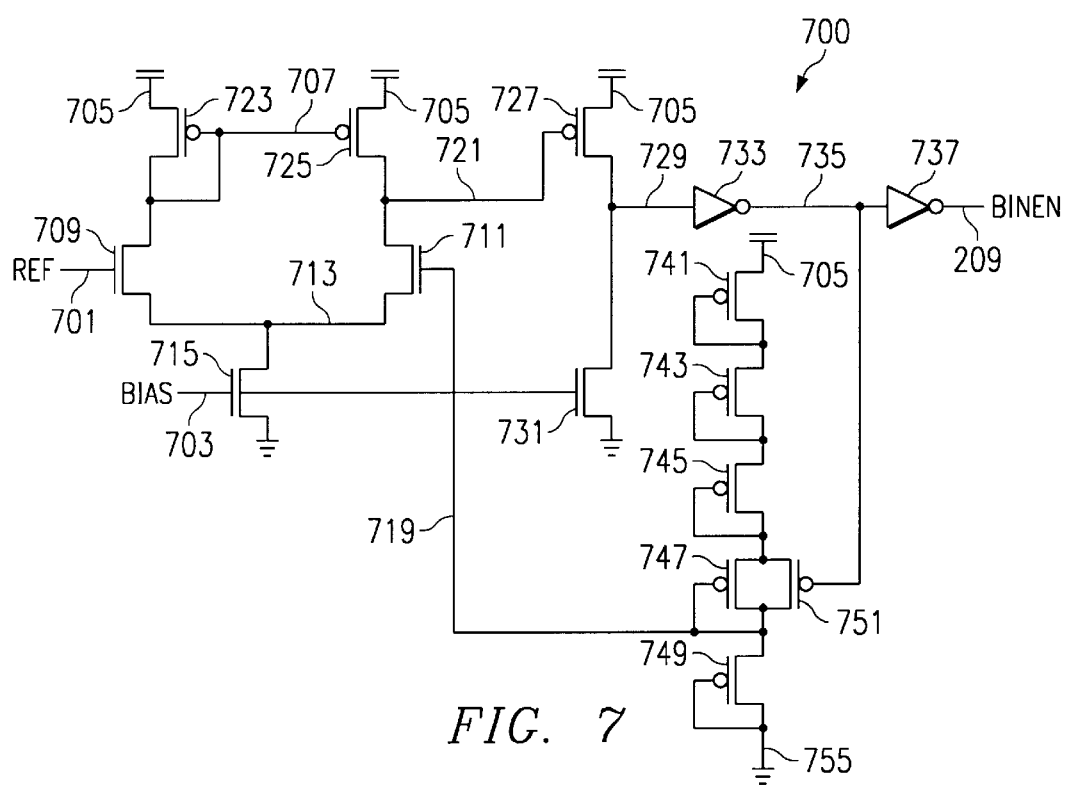
FIG. 7 is a level detector circuit that may be used with the present invention.

Turning now to FIG. 2, a control circuit for a column decode circuit will be explained in detail. A pulse control signal YPLS is produced on lead 201 by control logic 101 in synchronization with system clock signal CLK. Burn in enable signal BINEN on lead 209 is produced by the burn in detector circuit 700 (FIG. 7) of control logic 101. The burn in detector circuit includes a comparator circuit formed by current mirror transistors 723 and 725 and input transistors 709 and 711. The comparator circuit is enabled by signal BIAS on lead 703. A stable reference voltage REF is applied to the control gate of input transistor 709. A second input transistor 711 receives a sample on lead 719 of the external voltage supply at terminal 705. In normal operation, the external voltage at terminal 705 is less than the five P-channel threshold voltages of series-connected diodes 741, 743, 745 and 747. These series-connected diodes are off, so the sample signal on lead 719 is low. During a burn in condition, however, the external voltage on lead 705 is increased to 6.5 V, thereby increasing the level on lead 719. This increased level drives the comparator output signal on lead 721 low increasing the conductivity of buffer transistor 727. Buffer transistor 727 produces a high level output that is inverted by inverter 733. The low level from inverter 733 is applied to transistor 751, further increasing the sample voltage on lead 719. Inverter 737 receives the low level on lead 735 and produces burn in enable signal on lead 209. This burn in signal BINEN has a high level when a burn in mode is detected and a low level otherwise.

Figure 8A:
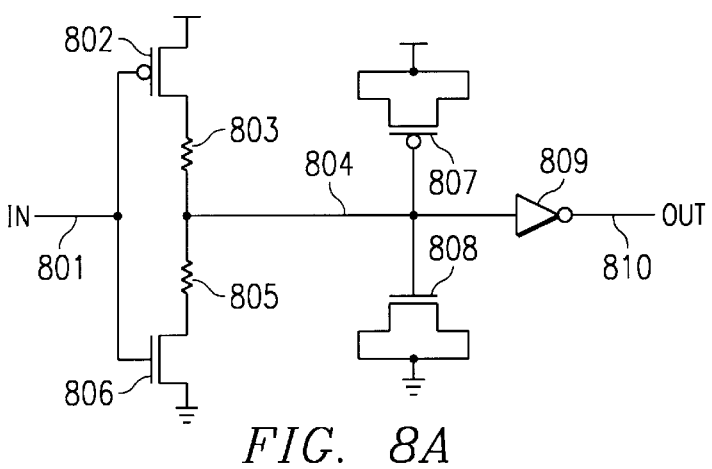
FIG. 8A is a delay circuit that may be used with the present invention.
Figure 8B:
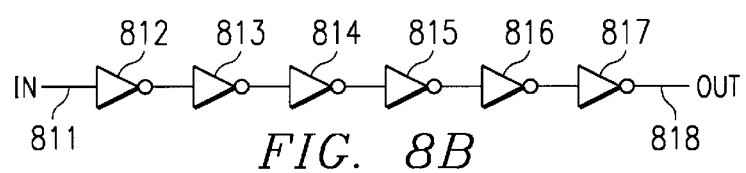
FIG. 8B is another delay circuit that may be used with the present invention.

A low level of burn in enable signal BINEN, therefore, turns on CMOS pass gate 203 (FIG. 2) and turns off CMOS pass gate 207 for normal operation, thereby conducting pulse control signal YPLS on lead 201 to pulse control signal YPLS' on lead 215 after a short delay. Alternatively, a high level of burn in enable signal BINEN turns on CMOS pass gate 207 and turns off CMOS pass gate 203 for burn in operation. During burn in operation, therefore, delay stage 205 and CMOS pass gate 207 conduct pulse control signal YPLS on lead 201 to pulse control signal YPLS' on lead 215 after a much greater delay established by delay stage 205. Delay circuit 205 may include series connected inverters (FIG. 8A) having a delay period determined by resistive and capacitive elements 803, 805 and 807, 808, respectively. Moreover, resistive element 805 may be designed with a resistance that is much less than the resistance of resistive element 803. Such asymmetrical resistance values provide a failing edge delay that is much greater than the rising edge delay, thereby increasing the pulse width of pulse control signal YPLS' over that of pulse control signal YPLS. Alternatively, delay circuit 205 may include series connected inverters 812–817 (FIG. 8B) as is well known in the art. The delayed pulse control signal YPLS' is applied to AND gate 219 together with address signal CAu to produce a pulsed predecode enable signal on lead 220.

The column decode circuit 115 (FIG. 2) includes multiple AND gates 227, 229 and 231. Each AND gate represents eight individual AND gates that are programmed with all binary combinations of respective column address signals CAr, CAs and CAt. For example, column address signal Car includes eight binary combinations of three address bits. The AND gates are enabled by the pulsed predecode enable signal on lead 220. The AND gates produce predecoded address signals on buses 233, 235 and 237. These predecoded address signals are applied to final column decode circuits 240 that produce column select signals YS on bus 243 for coupling a column of memory cells to a local data lead as will be explained in detail. This circuit is highly advantageous in producing a pulsed column select signal YS at a time determined by a detected operational mode. A column select signal YS for a normal mode is produced a short time after pulse control signal YPLS due to a minimal delay of CMOS pass gate 203. Alternatively, a column select signal YS for a burn in mode has a delay added by delay circuit 205 to compensate for increased circuit speed due to a high burn in voltage. Thus, circuit functionality is assured without compromise to optimal circuit performance under normal operating conditions.

Referring now to FIG. 3, there is a clock circuit having a timing circuit of the present invention. Pulse control signal YPLS' is applied to a first pulse generating circuit including delay circuit 303, inverter 305 and NAND gate 301. A low-to-high transition of pulse control signal YPLS' causes both inputs of NAND gate 301 to go high, thereby producing a low output on lead 307. This low output on lead 307 is maintained for a duration of delay circuit 303 and sets the flip-flop consisting of NAND gates 309 and 321 producing a latched high output on lead 311. After a time established by delay circuit 313, pulse control signal YPLS' causes both inputs of NAND gate 315 to go high, thereby producing a low output on lead 316. This low level resets the flip-flop, thereby producing a low level on lead 311. Thus, the signal on lead 311 is a high level pulse having a leading edge determined by pulse control signal YPLS' and a duration determined by delay circuit 313.

A low level of burn in enable signal BINEN for normal operation turns on CMOS pass gate 325, thereby conducting the signal on lead 311 to control signal IOCLK after a short delay. When a burn in mode is detected, however, burn in enable signal BINEN has a high level and turns on CMOS pass gate 327. Delay circuit 323 and CMOS pass gate 327, therefore, conduct the signal on lead 311 to control signal IOCLK after a greater delay determined by delay circuit 323. This circuit provides the same advantages as previously described and may be applied to any control circuit. Thus, control functions at any part of the circuit may be timed for a detected mode of operation to assure functionality without compromise to optimal performance under normal conditions.

Figure 4A:
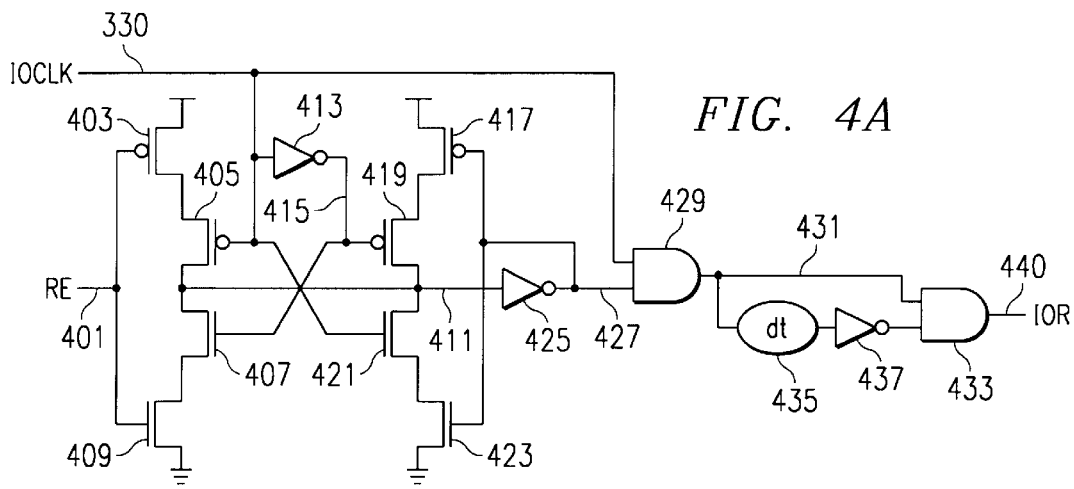
FIG. 4A is a schematic diagram of a read data latch circuit for generating a read control signal.
Figure 4B:
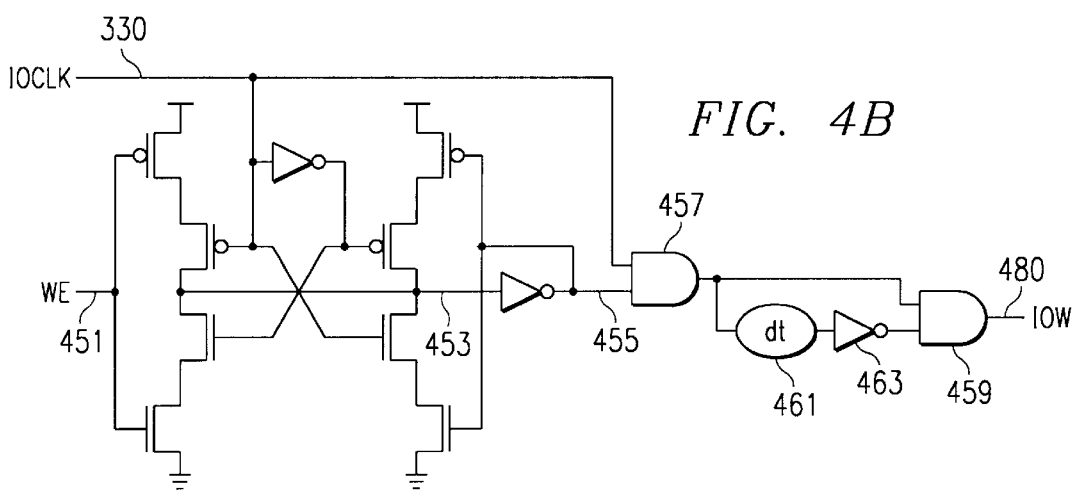
FIG. 4B is a schematic diagram of a write data latch circuit for generating a write control signal.

Control signal IOCLK is applied to the read control latch circuit of FIG. 4A to control timing of read control signal IOR. The write control latch circuit of FIG. 4B operates in the same manner, so only the read control latch will be described in detail. The read control latch includes two tristate inverters. The first tristate inverter, including transistors 403, 405, 407 and 409, receives read enable signal RE on lead 401. The output of this first tristate inverter is applied to inverter 425 while control signal IOCLK is low. Inverter 425 then produces a signal on lead 427 having the same phase as read control signal RE. The low level of control signal IOCLK turns off transistors 419 and 421 of the second tristate inverter.

A low-to-high transition of control signal IOCLK turns off transistors 405 and 407 and turns on transistors 419 and 421, thereby disabling the first tristate inverter and enabling the second. This second tristate inverter completes a latch formed with cross-coupled inverter 425, thereby maintaining the previous signal on lead 427. The high level of control signal IOCLK also enables AND gate 429 producing a low-to-high transition at the input terminal of a pulse generating circuit formed by delay circuit 435, inverter 437 and AND gate 433. This low-to-high transition causes both inputs of AND gate 433 to remain high for a time determined by delay circuit 435. Thus, read control signal IOR produces a high output pulse at a time determined by control signal IOCLK and having a duration established by delay circuit 435. This variable timing of read control signal IOR as determined by control signal IOCLK is based on a detected mode of operation to assure reliable circuit operation over a wide range of circuit parameters.

Figure 5:
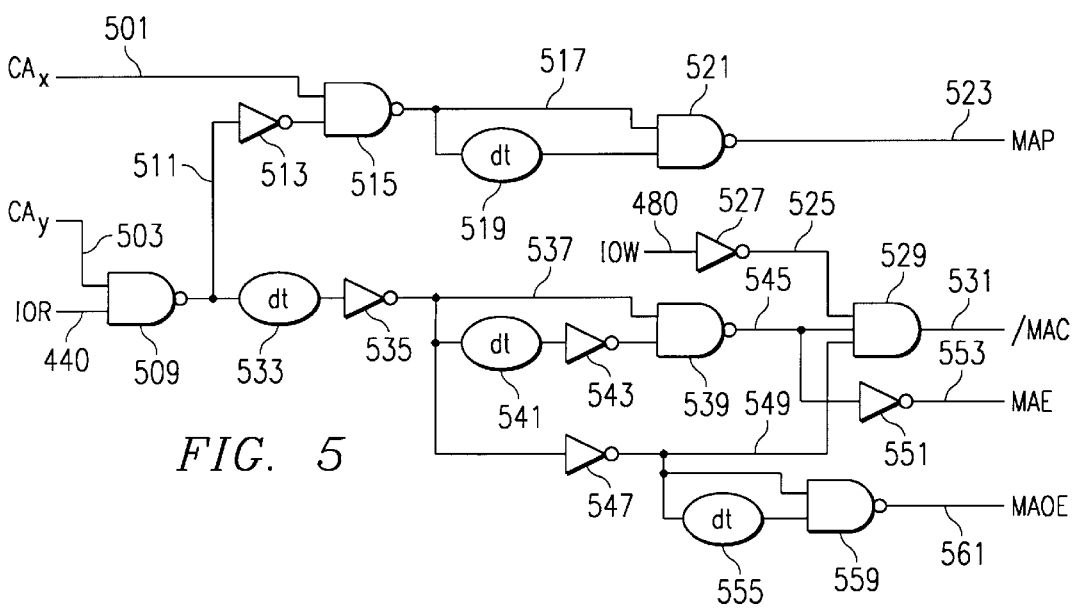
FIG. 5 is a schematic diagram of a control circuit for activating a data amplifier.
Figure 9A:
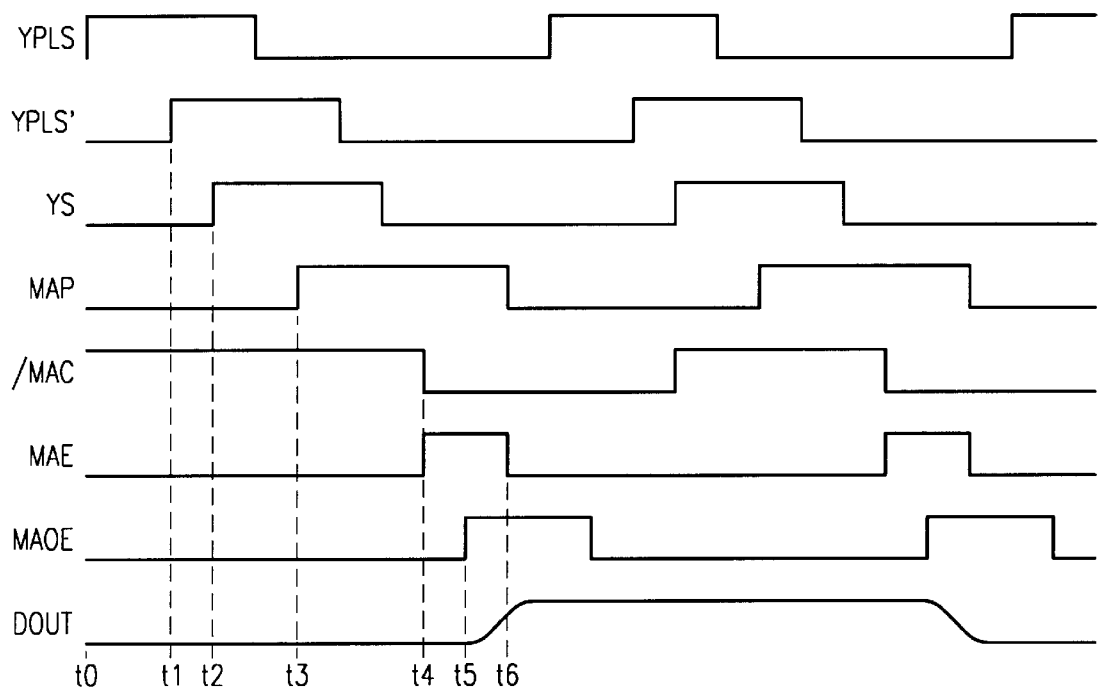
FIG. 9A is a timing diagram of a memory circuit using the present invention under burn in conditions.

The control circuit of FIG. 5 receives read control signal IOR on lead 440 and produces a sequence of control signals for activating a data amplifier. Operation of this circuit will be described in detail with reference to the simplified data path of FIG. 6 and the timing diagram of FIG. 9A. A low-to-high transition of pulse control signal YPLS at time t0 delays pulse control signal YPLS' until time t1 (FIG. 9A) in response to a high level of burn in enable signal BINEN as previously described. This pulse control signal YPLS' is applied to the column decode circuit (FIG. 2) to produce a column select signal on lead 243. The column select signal is applied to the control gates of select transistors 649 and 651. These select transistors couple complementary bit lines BL and /BL to data leads 661 and 663, respectively. Thus, a datum from a memory cell, for example memory cell 653, creates a differential voltage across complementary bit lines that is applied to data leads 661 and 663.

The control circuit of FIG. 5 is selected by column address signals CAx and CAy, respectively. In operation, high levels of address signal CAy and read control signal IOR produce a high level input signal at NAND gate 515. A high level of address signal CAx on lead 501 drives the output signal of NAND gate 515 low. This low level sends main amplifier precharge signal MAP high at time t3. The high level of main amplifier precharge signal MAP turns off precharge transistors 673, 675 and 679, leaving data input leads precharged to supply voltage Vdd. The high levels of main amplifier precharge signal MAP and main amplifier connect signal /MAC at the inputs of NAND gate 671 produce a low output on lead 669. This low level turns on transistors 665 and 667 which, in turn, apply the difference voltage on data leads 661 and 663 to input leads 683 and 681, respectively, of the data amplifier 670.

After a sufficient difference voltage is developed at the inputs of the data amplifier 670, column select signal YS goes low. This low level isolates the complementary bit lines BL and /BL from the parasitic capacitance of the data leads 661 and 663. This isolation permits sense amplifier 643 to quickly restore the datum of memory cell 653 before word line 657 returns low.

Figure 6:
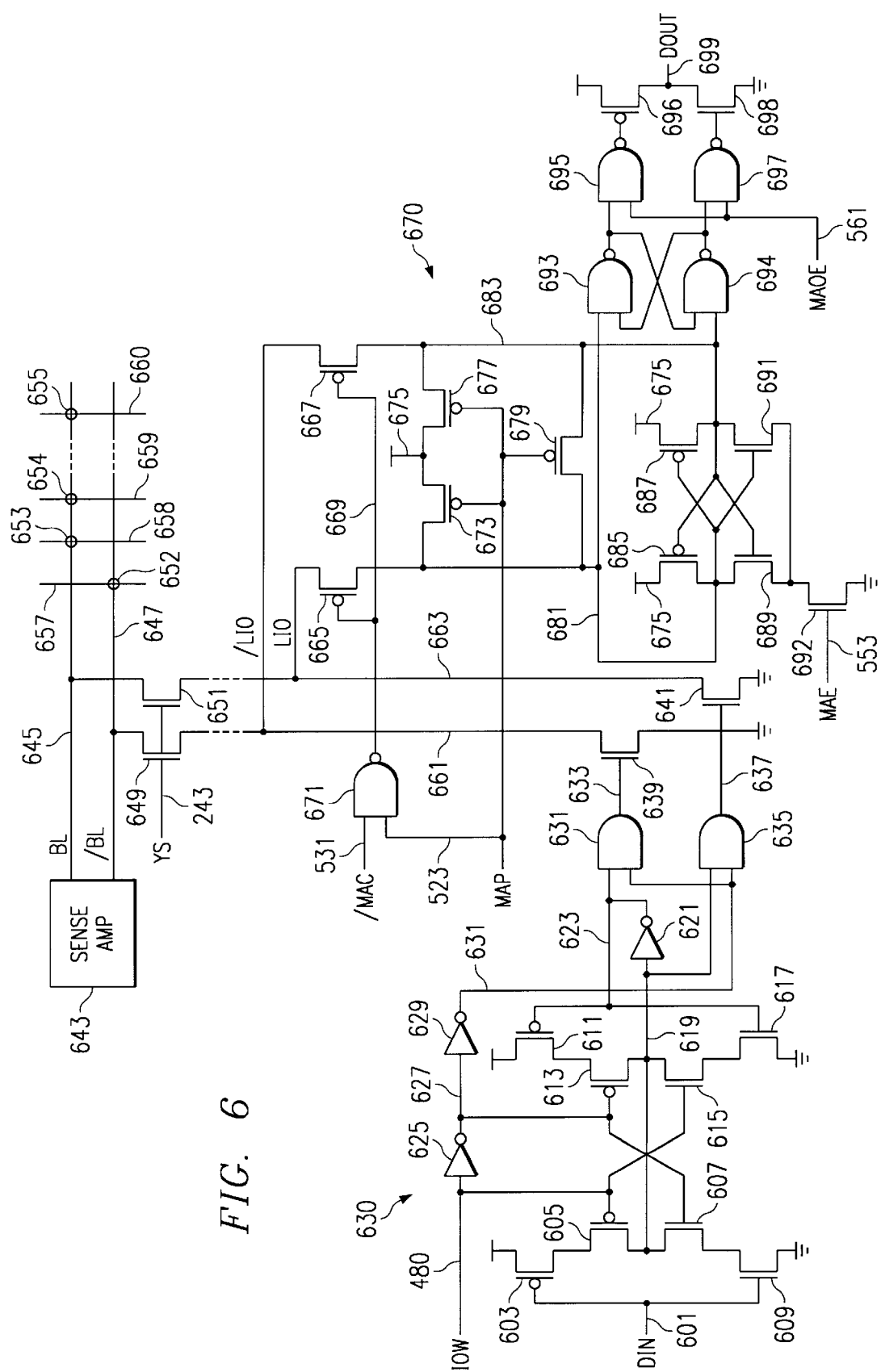
FIG. 6 is a simplified schematic diagram showing a data path of a memory circuit having control signals produced by the present invention.

A delayed version of read control signal IOR and address signal CAy is applied to a pulse generating circuit formed by delay circuit 541, inverter 543 and NAND gate 539 via delay circuit 533 and inverter 535. This pulse generating circuit produces a low level pulse having a duration corresponding to delay circuit 541. Consequently, AND gate 529 produces a low level main amplifier connect pulse /MAC at time t4. This low level main amplifier connect pulse /MAC is applied to NAND gate 671, thereby turning off transistors 665 and 667. A differential voltage from data leads 661 and 663 between times t3 and t4, therefore, is trapped on data amplifier input leads 683 and 681. Inverter 551 produces main amplifier enable signal MAE on lead 553 corresponding to the low level pulse from NAND gate 539. This main amplifier enable signal MAE turns on transistor 692 and latches the data amplifier 670 in a data state corresponding to the trapped differential voltage on the input data leads. The latched state of the data amplifier is stored in a flip-flop formed by NAND gates 693 and 694. At time t5, NAND gate 559 produces a high main amplifier output enable signal MAOE in response to the low level on lead 549. This high level enables NAND gate 695 and AND gate 697 (FIG. 6). Subsequently, NAND gate 695 and AND gate 697 apply the latched datum at the flip-flop formed by NAND gates 693 and 694 to output transistors 696 and 698, thereby producing valid output data at time t6.

Figure 9B:
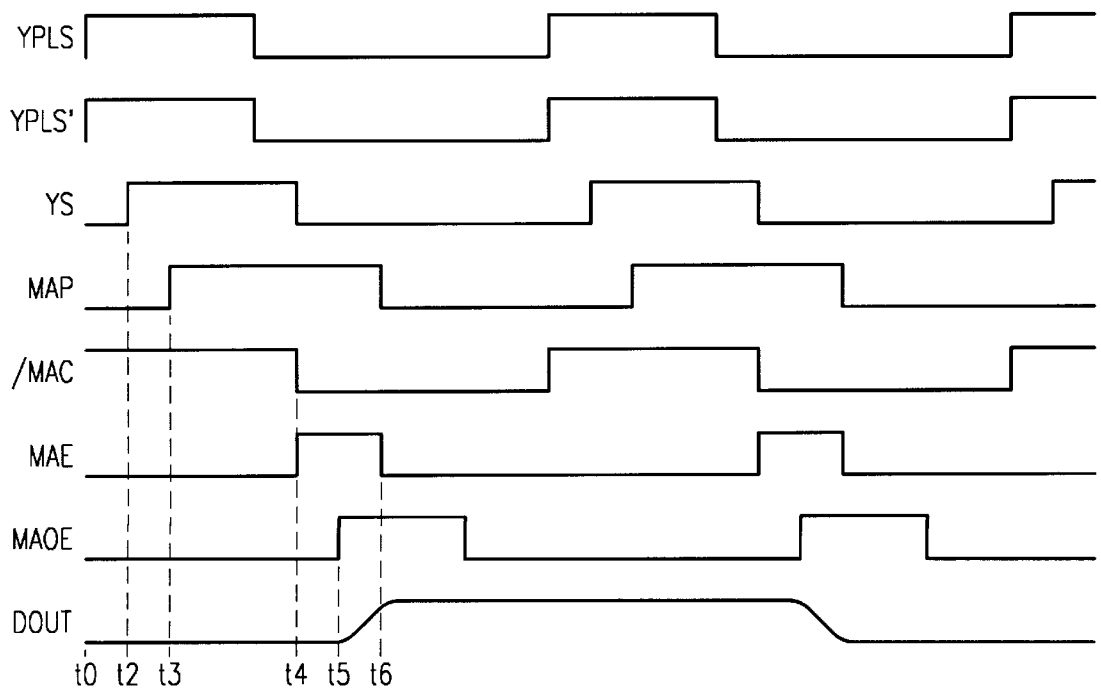
FIG. 9B is a timing diagram of a memory circuit using the present invention under normal conditions.

A comparison of the normal mode timing diagram (FIG. 9B) with the burn in timing diagram (FIG. 9A) reveals a significant advantage of the present invention. Pulse control signals YPLS and YPLS' both occur substantially at time t0 for normal mode. An optimal low-to-high transition of column select signal YS for normal mode, therefore, is only delayed for a burn in mode of operation. This delayed operation compensates for faster circuit operation at a burn in voltage of 6.5 V. This delayed operation provides sufficient time for the sense amplifier to amplify a difference voltage across complementary bit lines BL and /BL prior to connection to high capacitance data leads. Furthermore, optimal control circuit timing for activating the data amplifier under normal operating conditions would be much too fast for burn in conditions. Thus, an additional delay of main amplifier control signals MAP, /MAC, MAE and MAOE assures functionality under burn in conditions.

Write control circuit operation is delayed for burn in operation by adding delay to write control signal IOW. The write control latch circuit 630 (FIG. 6) operates in the same manner as the read control latch of FIG. 4A. In operation, the write control latch circuit produces a high level pulse IOW at a time determined by control signal IOCLK and having a duration corresponding to delay circuit 461. This high level of write control signal IOW produces a low level at an input terminal of AND gate 529 (FIG. 5), producing a low level main amplifier connect signal /MAC. This low level of main amplifier connect signal /MAC applied to NAND gate 671 (FIG. 6) turns off transistors 665 and 667, thereby isolating the read data amplifier 670 from data leads 661 and 663. The high level of write control signal IOW also activates data latch 630 and enables AND gates 631 and 635. The enabled AND gates subsequently drive transistors 639 and 641 according to the data state of data latch 630. Thus, one of transistors 639 and 641 will override sense amplifier 643 and write a new datum into memory cell 653.

Although the invention has been described in detail with reference to its preferred embodiment, it is to be understood that this description is by way of example only and is not to be construed in a limiting sense. For example, additional delay might be incorporated in any control circuit to compensate for a change of operating conditions. For example, additional delay might be incorporated in an address path to provide time for correct addresses to propagate to decode or redundancy circuits during a burn in mode. Moreover, timing delays may be adjusted for any detectable mode of operation that would alter circuit speed. Finally, a reduced delay circuit might even be designed to gain circuit speed for low voltage operation.

It is to be further understood that numerous changes in the details of the embodiments of the invention will be apparent to persons of ordinary skill in the art having reference to this description. It is contemplated that such changes and additional embodiments are within the spirit and true scope of the invention as claimed below.

What is claimed:

1. A circuit, comprising:
   a detector circuit coupled between a supply voltage terminal and a reference voltage terminal, the detector circuit producing a first control signal in response to a detected mode and producing a second control signal in response to another mode;
   a delay circuit coupled to receive the first control signal and a third control signal, the delay circuit producing a fourth control signal at an output terminal at a first time in response to the first and third control signals; and
   a logic circuit coupled to receive the second control signal and the third control signal, the logic circuit producing the fourth control signal at the output terminal at a second time different from the first time in response to the second and third control signals.

2. A circuit as in claim 1, wherein the detected mode is a burn in mode.

3. A circuit as in claim 1, wherein the detector circuit produces the first and second control signals at a detector output terminal, the first control signal having a first level and the second control signal having a second level.

4. A circuit as in claim 1, further comprising a transistor having a control gate coupled to receive the fourth control signal, the transistor having a current path coupled between a first data lead and a second data lead.

5. A circuit as in claim 4, further comprising a memory cell coupled to the first data lead, the memory cell arranged to produce a datum on the first data lead.

6. A circuit as in claim 5, further comprising a data amplifier coupled to the second data lead.

7. A circuit as in claim 6, wherein the data amplifier is activated in response to the fourth control signal, the data amplifier amplifying the datum after the first time in response to the first control signal and amplifying the datum after the second time in response to the second control signal.

8. A circuit, comprising:
   a detector circuit coupled between a supply voltage terminal and a reference voltage terminal, the detector circuit producing a first control signal;
   a first switching circuit including a delay circuit, the first switching circuit producing a second control signal at a first time in response to a first level of the first control signal, the first switching circuit not producing the second control signal response to a second level of the first control signal; and
   a second switching circuit arranged to produce the second control signal at a second time different from the first time in response to the second level of the first control signal, the second switching circuit not producing the second control signal in response to the first level of the first control signal.

9. A circuit as in claim 8, wherein the detector circuit produces the first control signal in response to a voltage between the supply voltage terminal and the reference terminal.

10. A circuit as in claim 8, wherein the second control signal is a pulse.

11. A circuit as in claim 8, further comprising a transistor having a control gate coupled to receive the second control signal from one of the first and second switching circuits, the transistor having a current path coupled between a first data lead and a second data lead.

12. A circuit as in claim 11, further comprising a memory cell coupled to the first data lead, the memory cell arranged to produce a datum on the first data lead.

13. A circuit as in claim 12, further comprising a sense amplifier coupled to the first data lead.

14. A circuit as in claim 12, further comprising a data amplifier coupled to the second data lead.

15. A circuit as in claim 14, wherein the data amplifier is activated in response to the second control signal, the data amplifier amplifying the datum after the first time in response to the first level and amplifying the datum after the second time in response to the second level.

16. A circuit, comprising:
   a mode select circuit coupled between a supply voltage terminal and a reference voltage terminal, the mode select circuit producing a control signal having a first level in response to a detected mode and having a second level in response to another mode; and
   a logic circuit coupled to receive an input signal at a first time and the control signal, the logic circuit producing an output signal at a second time after the first time in response to the first level of the control signal, the logic circuit producing the output signal at a third time after the first time and different from the second time in response to the second level of the control signal.

17. A circuit as in claim 16, wherein a high voltage produces the first level and a normal voltage produces the second level.

18. A circuit as in claim 16, further comprising a transistor having a control gate coupled to receive the output signal, the transistor having a current path coupled between a memory cell and a data lead.

19. A circuit as in claim 18, wherein the memory cell is a dynamic random access memory cell.

20. A circuit as in claim 16, further comprising a data amplifier coupled to a data lead and coupled to receive the control signal, wherein the data amplifier is activated in response to the control signal thereby amplifying a datum after the first time in response to the first level and amplifying the datum after the second time in response to the second level.

21. A circuit, comprising:
   a mode select circuit coupled between a supply voltage terminal and a reference voltage terminal, the mode select circuit producing a control signal having a first level in response to a detected mode and having a second level in response to another mode; and
   a logic circuit coupled to receive an input signal having a first pulse width at a first time and the control signal, the logic circuit producing an output signal having substantially the first pulse width after the first time in response to the first level of the control signal, the logic circuit producing the output signal having a second pulse width at a second time in response to the second level of the control signal.

22. A circuit as in claim 21, wherein the second pulse width is greater than the first pulse width.

23. A circuit as in claim 22, wherein the second time is after said after the first time.

24. A circuit as in claim 21, further comprising a transistor having a control gate coupled to receive the output signal, the transistor having a current path coupled between a memory cell and a data lead.

25. A circuit as in claim 24, wherein the memory cell is a dynamic random access memory cell.

26. A circuit as in claim 22, further comprising a data amplifier coupled to a data lead and coupled to receive the control signal, wherein the data amplifier is activated in response to the control signal thereby amplifying a datum in response to the output signal having said substantially the first pulse width and amplifying the datum in response to said output signal having the second pulse width.

27. A method of operating a circuit comprising the steps of:
   producing a first logic state of a delay signal in a first mode;
   applying the first logic state of the delay signal and a control signal to a logic circuit;
   producing an output signal delayed by a first time at an output terminal of the logic circuit in response to the control signal and the first logic state of the delay signal;
   producing a second logic state of the delay signal in a second mode;
   applying the second logic state of the delay signal and the control signal to the logic circuit;
   producing the output signal delayed by a second time different from the first time at the output terminal of the logic circuit in response to the control signal and the second logic state of the delay signal; and operating the circuit in response to the output signal.

28. A method of operating a circuit as in claim 27, comprising the step of detecting the first mode in response to a level of a supply voltage.

29. A method of operating a circuit as in claim 27, wherein the second time is less than the first time.

30. A method of operating a circuit as in claim 27, wherein the output signal is a pulse and wherein the pulse has a first width in response to the first logic state and wherein the pulse has a second width different from the first width in response to the second logic state.

31. A method of operating a circuit as in claim 27, wherein the step of operating comprises enabling a data path of the circuit.

32. A method of operating a circuit as in claim 27, wherein the step of operating comprises enabling an address path of the circuit.

33. A method of operating a circuit as in claim 27, wherein the first mode is a test mode and wherein the second mode is a normal mode.

* * * * *